US012157228B2

(12) United States Patent
Takagi et al.

(10) Patent No.: US 12,157,228 B2
(45) Date of Patent: Dec. 3, 2024

(54) CONTINUUM ROBOT AND CONTINUUM ROBOT CONTROL SYSTEM

(71) Applicant: CANON KABUSHIKI KAISHA, Tokyo (JP)

(72) Inventors: Kiyoshi Takagi, Tokyo (JP); Yusuke Tanaka, Tokyo (JP); Hidekazu Kose, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 947 days.

(21) Appl. No.: 17/095,619

(22) Filed: Nov. 11, 2020

(65) Prior Publication Data

US 2021/0060800 A1 Mar. 4, 2021

Related U.S. Application Data

(63) Continuation of application No. PCT/JP2019/018845, filed on May 11, 2019.

(30) Foreign Application Priority Data

May 17, 2018 (JP) .................................. 2018-095568

(51) Int. Cl.
   *B25J 9/16* (2006.01)
   *A61B 1/005* (2006.01)
   (Continued)

(52) U.S. Cl.
   CPC .............. *B25J 9/1635* (2013.01); *A61B 1/005* (2013.01); *B25J 9/065* (2013.01); *B25J 9/104* (2013.01);
   (Continued)

(58) Field of Classification Search
   CPC . B25J 9/1635; B25J 9/065; B25J 9/104; B25J 18/06; B25J 9/06; B25J 9/1625;
   (Continued)

(56) References Cited

U.S. PATENT DOCUMENTS

| 9,956,042 B2* | 5/2018 | Simaan | A61B 34/74 |
| 2005/0101836 A1* | 5/2005 | Onuki | A61M 25/09 |
| | | | 600/104 |

(Continued)

FOREIGN PATENT DOCUMENTS

| JP | H01177988 A | 4/1989 |
| JP | 2017121472 A | 7/2017 |

(Continued)

OTHER PUBLICATIONS

Kai Xu, et al., An Experimental Kinestatic Comparison between Continuum Manipulators with Structural Variations, IEEE International Conference on Robotics and Automation (ICRA), Hong Kong, China, 2014, pp. 3258-3264.

*Primary Examiner* — Adam R Mott
*Assistant Examiner* — Sagar Kc
(74) *Attorney, Agent, or Firm* — Canon U.S.A., Inc. IP Division

(57) ABSTRACT

A continuum robot includes: a first wire; a second wire; a distal guide configured to hold the first wire and the second wire; a proximal guide slidable relative to the first wire and the second wire; a plurality of wire guides provided between the distal guide and the proximal guide; a driving unit configured to drive the first wire and the second wire; and a control unit configured to control the driving unit. The first wire is fixed to the plurality of wire guides, the second wire is slidable relative to the plurality of wire guides, and the control unit controls the driving unit so as to keep a distance between the proximal guide and a wire guide among the plurality of wire guides provided nearest to the proximal guide constant.

2 Claims, 10 Drawing Sheets

(51) Int. Cl.
*B25J 9/06* (2006.01)
*B25J 9/10* (2006.01)
*B25J 18/06* (2006.01)
*G05B 19/4155* (2006.01)

(52) U.S. Cl.
CPC .......... *B25J 18/06* (2013.01); *G05B 19/4155* (2013.01); *G05B 2219/50391* (2013.01)

(58) Field of Classification Search
CPC .... A61B 1/005; A61B 1/008; G05B 19/4155; G05B 2219/50391; G05B 2219/40234; G05B 2219/40279; G02B 23/24
See application file for complete search history.

(56) References Cited

U.S. PATENT DOCUMENTS

| | | | |
|---|---|---|---|
| 2013/0131868 A1* | 5/2013 | Rucker | B25J 9/1625 700/262 |
| 2016/0016319 A1 | 1/2016 | Remirez et al. | |
| 2017/0361470 A1* | 12/2017 | Otero Del Real | B25J 18/02 |

FOREIGN PATENT DOCUMENTS

| | | |
|---|---|---|
| JP | 2018008335 A | 1/2018 |
| JP | 2018171701 A | 11/2018 |

* cited by examiner

CONTINUUM ROBOT AND CONTINUUM ROBOT CONTROL SYSTEM

CROSS-REFERENCE TO RELATED APPLICATIONS

This application is a Continuation of International Patent Application No. PCT/JP2019/018845, filed May 11, 2019, which claims the benefit of Japanese Patent Application No. 2018-095568, filed May 17, 2018, both of which are hereby incorporated by reference herein in their entirety.

BACKGROUND OF THE INVENTION

Field of the Invention

The present invention relates to a continuum robot and a continuum robot control system.

Background Art

Continuum robots are also called continuum robots and formed of a plurality of bending sections having a flexible structure, and the bending sections are deformed to thereby control the form. Robots of this type mainly have two advantages over robots formed of rigid links. First, continuum robots can move along a curved line in a narrow space or in an environment littered with things where rigid-link robots may be stuck. Second, continuum robots are soft by their nature and can move within a fragile target object without causing damage to the target object. Accordingly, for example, detection of external force, which is necessary for rigid-link robots, might not be necessary. By taking advantage of such characteristics, application to endoscope sheaths and catheters used in the medical field and to robots for hazardous environments, such as rescue robots, is anticipated. Examples of a method for driving continuum robots include a tendon driving method, a method using push-pull wires, and a method using air actuators. NPL1 discloses a continuum robot formed of three wires, wire guides called spacer disks that guide the wires, a distal end called an end disk, and a base part. Kinematics are derived to calculate the push-pull driving amounts of the wires, thereby controlling the form of the continuum robot. In the robot described in NPL1, holes through each of which a wire passes are provided along the circumference of each wire guide. The wires are configured to be fixed only to the end disk, which is the distal end, and to slide relative to the wire guides provided between the base part and the end disk.

CITATION LIST

Non Patent Literature

NPL1: K. Xu, M. Fu, and J. Zhao, "An Experimental Kinestatic Comparison between Continuum Manipulators with Structural Variations", in IEEE International Conference on Robotics and Automation (ICRA), Hong Kong, China, 2014, pp. 3258-3264.

In NPL1, in a case of deriving kinematics for expressing a motion of the continuum robot, it is assumed that the wires deform at a uniform curvature, and the driving amounts of the wires are calculated such that the length of a virtual wire that passes through the center of the continuum robot is kept constant regardless of the form of the continuum robot. However, when the positions of the wire guides shift due to sliding friction between, for example, the wires and the wire guides caused by driving of the wires, the wire curvatures become non-uniform, and an error relative to the kinematics, which assume that the wire curvatures are uniform, becomes large. Accordingly, the accuracy of form control might become unsatisfactory.

In view of the above-described issue, an object of the present invention is to increase the accuracy of control of a continuum robot.

SUMMARY OF THE INVENTION

In order to address the above-described issue, a continuum robot according to an aspect of the present invention is characterized by including: a first wire; a second wire; a distal guide configured to hold the first wire and the second wire; a proximal guide slidable relative to the first wire and the second wire; a plurality of wire guides provided between the distal guide and the proximal guide; a driving unit configured to drive the first wire and the second wire; and a control unit configured to control the driving unit. The first wire is fixed to the plurality of wire guides, the second wire is slidable relative to the plurality of wire guides, and the control unit controls the driving unit so as to keep a distance between the proximal guide and a wire guide among the plurality of wire guides provided nearest to the proximal guide constant.

A continuum robot control system according to another aspect of the present invention is characterized by including: a continuum robot including a first wire and a second wire extending relative to a reference plane, a first wire guide to which the first wire and the second wire are fixed at different positions, and a second wire guide provided between the reference plane and the first wire guide and configured to guide the first wire and the second wire, the continuum robot having a bending section bendable by driving at least one of the first wire and the second wire; and a first calculation unit configured to calculate a first driving displacement amount of at least one of the first wire and the second wire in accordance with input of a desired bending angle that is a desired value of a bending angle of the bending section and a desired rotation angle that is a desired value of a rotation angle of the bending section. The first wire is fixed to the second wire guide, and the continuum robot control system is characterized by further including: a second calculation unit configured to calculate a second driving displacement amount of at least one of the first wire and the second wire in accordance with a desired distance between the reference plane and a proximal end that is an end part of the second wire guide on a side nearer to the reference plane; and an addition unit configured to add up the first driving displacement amount and the second driving displacement amount.

Further features of the present invention will become apparent from the following description of exemplary embodiments with reference to the attached drawings.

DESCRIPTION OF THE EMBODIMENTS

Hereinafter, embodiments of the present invention will be described in detail with reference to the drawings. In the embodiments, an example is given where a continuum robot (also called continuum manipulator) control system is applied to a flexible endoscope. Note that the flexible endoscope, which is an example, to which the continuum robot control system according to the embodiments of the present invention is applied is applicable not only to the medical field but also to the other fields as long as the flexible endoscope is used to observe the inside of passages (hereinafter referred to as "insertion-withdrawal passages") into and from which its bending section is inserted and withdrawn (for example, an industrial endoscope for observing the inside of, for example, pipes).

First Embodiment

In this embodiment, a control system is described in which the kinematics of a continuum robot capable of controlling its form in three dimensions by driving three wires are derived to keep the distance between the most proximal wire guide and a base part constant.

Derivation of the kinematics of the continuum robot and a control algorithm are described in detail below.

1.1) Modeling

Figure 1:
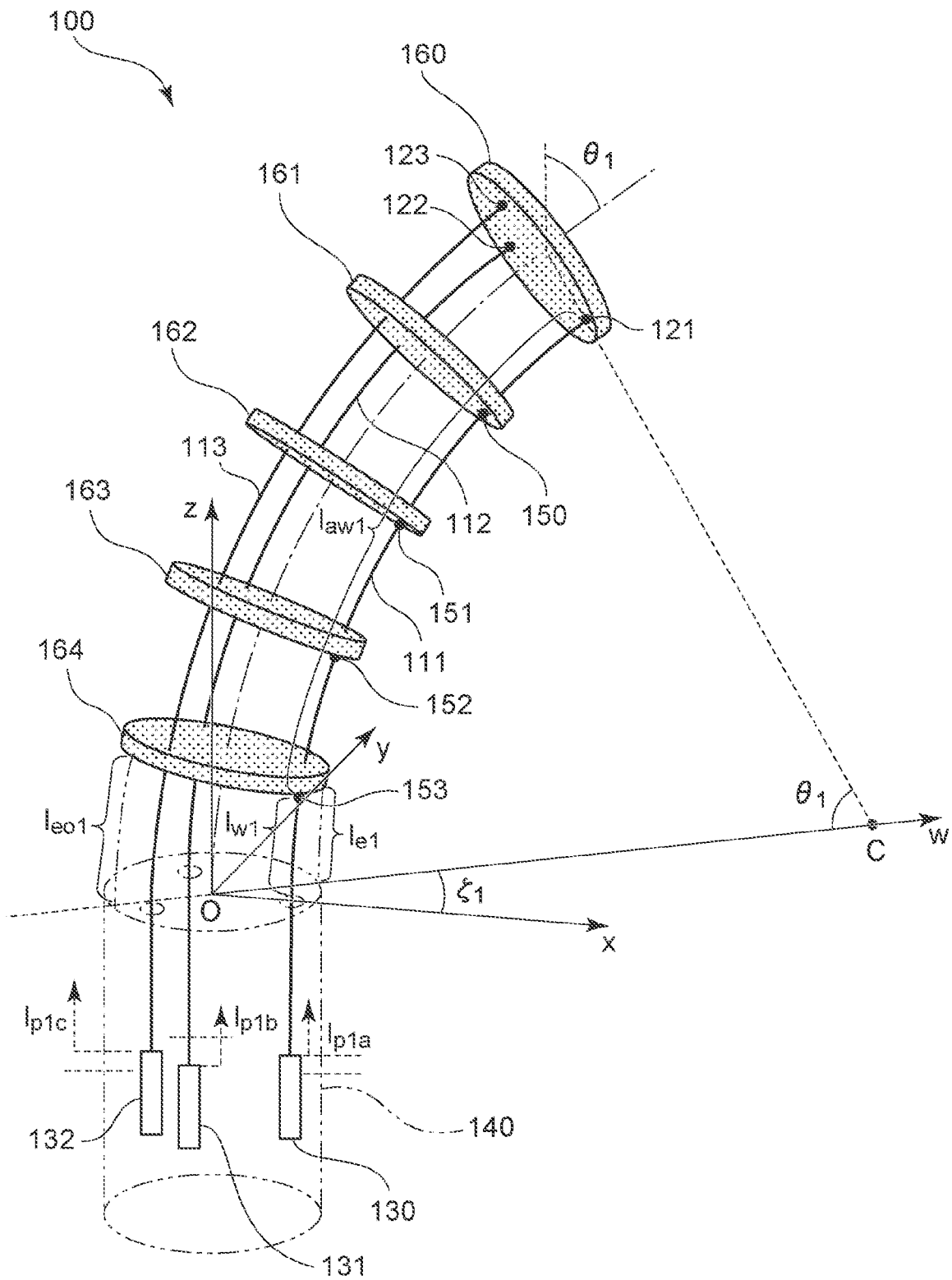
FIG. 1 is a diagram illustrating a kinematic model of a continuum robot according to a first embodiment.
Figure 2:
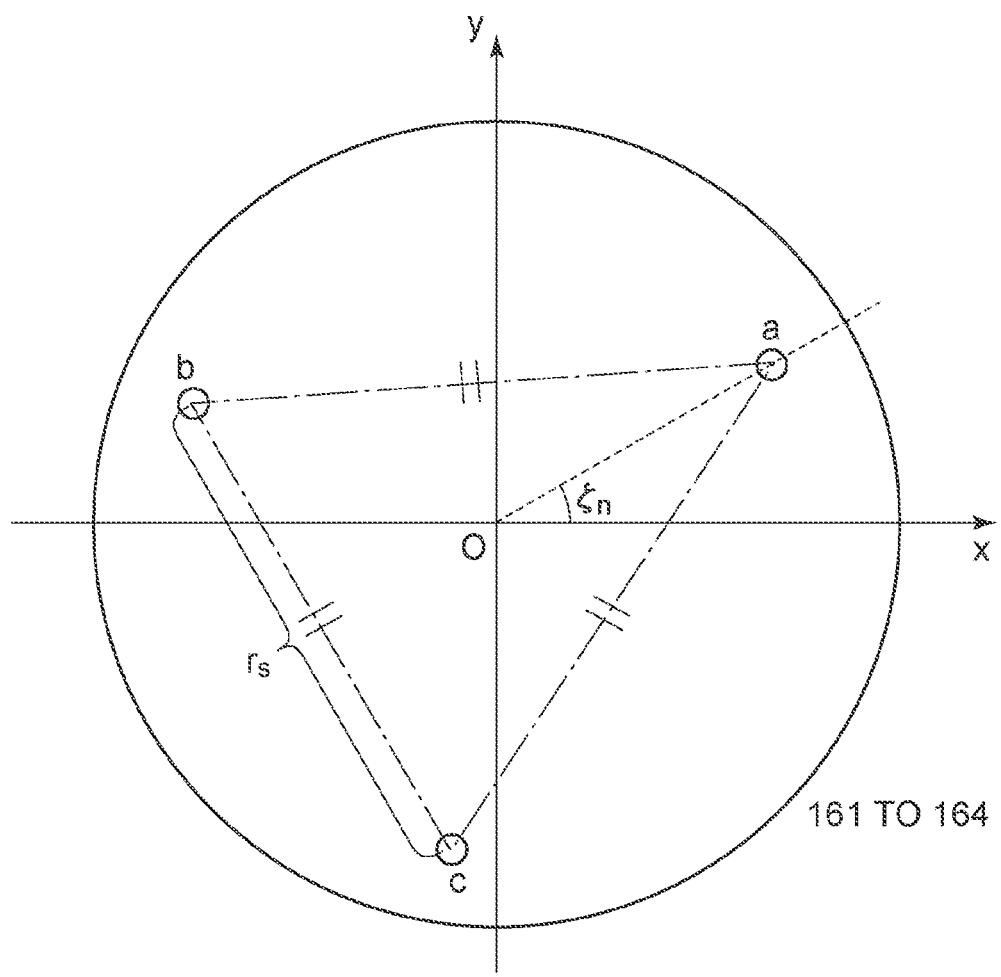
FIG. 2 is a diagram for describing the kinematic model of the continuum robot according to the first embodiment.

FIG. 1 is a schematic diagram of a continuum robot 100 used in this embodiment. Here, an example where the continuum robot 100 has one bending section is given. Wires 111 to 113 are connected to a distal wire guide (hereinafter also referred to as a distal guide) 160 provided at the distal end of the bending section of the continuum robot 100 at connection portions 121 to 123 respectively. The continuum robot 100 includes wire guides 161 to 164 that are members for guiding the wires 111 to 113. The wire guide 164 provided nearest to the base end side (proximal side) is also called a proximal wire guide or a proximal guide. The wire guides 160 to 164 are illustrated as disk-shaped members but are not limited to this example, and may be, for example, ring-shaped members. The wire guides 160 to 164 are configured as wire guides having an opening in an area that includes the central axis of the continuum robot 100 represented by a dashed line, thereby allowing a tool, such as a camera, to be introduced into the openings. In addition to the method of discretely arranging the plurality of wire guides as in this example, for example, a bellows or mesh continuum member may be used as the wire guides. The wire guides 161 to 164 are fixed to the wire 111 at fixing portions 150 to 153 respectively. The wires 112 and 113 are configured so as to be slidable relative to the wire guides 161 to 164. In the description, the wire 111 fixed to the wire guides are called a-wire, and the wires 112 and 113 are respectively called b-wire and c-wire counterclockwise from a-wire on the xy plane, where a-wire corresponds to a first wire, and b-wire and c-wire each correspond to a second wire. The lengths of the wires 111 to 113 in the xyz space are represented by $l_{1a}$, $l_{1b}$, and $l_{1c}$ respectively. The driving displacements of the wires that drive the bending section are represented by $l_{p1a}$, $l_{p1b}$, and $l_{p1c}$ respectively. As illustrated in FIG. 2, the wires are arranged at the respective vertexes of a regular triangle, a side of which has a length $r_s$, and a phase angle $\xi_1$ is an angle that determines the arrangement of the wires that drive the first bending section. In this embodiment, $\xi_1=0$ is assumed. Note that FIG. 2 is a plan view of any of the wire guides 161 to 164 placed on the xy plane and viewed from the distal end side toward the proximal end of the continuum robot 100.

When the wires 111 to 113 are push-pull driven by actuators 130 to 132 that are driving units provided in a robot base part 140, the bending section, that is, the posture of the continuum robot 100, can be controlled. The robot base part 140 has openings through which the wires 111 to 113 are inserted. In other words, the robot base part 140 includes a wire guide. The surface of the robot base part 140 can be assumed to be a reference plane.

The following are the definitions of symbols: $l_{1d}$: the initial length of the central axis of the bending section (the length of the central axis in a case where the continuum robot is not bending); $\theta_1$: the bending angle of the distal end (the angle made by a direction normal to the distal wire guide with the z axis in the figure); $\zeta_1$: the rotation angle of the distal end; $\rho_1$: the radius of curvature of the bending section; r: the radius of the wire guides; $l_{1a}$: the length of a-wire in the xyz space; $l_{aw1}$: the distance from the tip of a-wire to the base-end-side surface of the wire guide nearest to the base end side, on a-wire; $l_{w1}$: the distance from the base-end-side surface of the wire guide nearest to the base end side to the xy plane, on a-wire; $l_{e1}$: the distance from the base-end-side surface of the wire guide nearest to the base end side to the xy plane, on an arc of a circle centered at the point C in the wz plane and having a radius of $\rho_1-r$ (this is called a proximal minimum gap length in the present invention); and $l_{eo1}$: the distance from the base-end-side surface of the wire guide nearest to the base end side to the xy plane, on an arc of a circle centered at the point C in the wz plane and having a radius of $\rho_1+r$ (this is called a proximal maximum gap length in the present invention).

The following are assumed, and the kinematics of the continuum robot are derived.

[1] In the bending section, the wires deform such that the curvatures are constant.

[2] Twisting deformation of the wires is not taken into consideration.

[3] The wires do not deform in the longitudinal direction.

[4] Friction between the wire guides and the wires is not taken into consideration.

To set the bending angle and the rotation angle of the distal end to $\theta_1$ and $\zeta_1$ respectively, candidates for the driving displacements $l_{p1a}$, $l_{p1b}$, and $l_{p1c}$ of a-, b-, and c-wires in the first bending section are expressed as follows.

[Math. 1]

$$l_{p1a} = -\frac{r_s}{\sqrt{3}}\cos(\zeta_1 - \xi_1)\theta_1 \quad (1)$$

$$l_{p1b} = -\frac{r_s}{\sqrt{3}}\cos\left(\frac{2\pi}{3} - \zeta_1 + \xi_1\right)\theta_1$$

$$l_{p1c} = -\frac{r_s}{\sqrt{3}}\cos\left(\frac{4\pi}{3} - \zeta_1 + \xi_1\right)\theta_1$$

Here, when, for example, the wire guides 160 to 164 are arranged at regular intervals as illustrated in FIG. 1, the wire guides are fixed to a-wire, and therefore, the maximum driving displacement of a-wire in the negative direction when the rotation angle satisfies $\zeta_1=0$ is limited to $$-(l_{1d}-5t_{wg})/5$$

or below, where $t_{wg}$ is the thickness of the wire guides. The maximum angle of bending changes relative to the rotation angle $\zeta_1$. Further, the distance from the base end to the base end side of the wire guide 164 changes as the rotation angle $\zeta_1$ changes. Therefore, in a case where the continuum robot 100 is equipped with, for example, a resin tube that covers the bending section of the continuum robot as a protective structure, the expansion-contraction amount of the protective structure between the base end and the base end side of the wire guide also changes relative to the rotation angle to the rotation angle $\zeta_1$. Accordingly, the protective structure is required to sufficiently expand and contract so as to respond to changes in the distance from the base end to the base end side of the wire guide 164. As a result, there is concern that the choices of a material that can be employed as the protective structure are limited.

Accordingly, in this embodiment, control is performed so as to keep the proximal minimum gap length $l_{e1}$ constant regardless of the rotation angle $\zeta_1$. This length is expressed as follows when the bending angle $\theta_1$ is positive.

[Math. 2]

$$l_{e1} = (\rho - r)\theta_1 \frac{l_{w1}}{l_{1a}} \quad (2)$$

$$= (l_{1d} - r\theta_1)\frac{l_{1d} + l_{p1a} - l_{aw}}{l_{1d} + l_{p1a}}$$

The length is expressed as follows when the bending angle $\theta_1$ is negative.

[Math. 3]

$$l_{e1} = (l_{1d} + r\theta_1)\frac{l_{1d} + l_{p1a} - l_{aw}}{l_{1d} + l_{p1a}} \quad (3)$$

1.2) Control System Design

Now, a control system for controlling the continuum robot 100 is described. Here, the driving displacements of the respective wires are calculated on the basis of a desired form, that is, a desired posture, of the continuum robot, and a driving displacement for keeping the distance between the wire guide and the base part constant is also calculated. Then, an algorithm for adding the driving displacement is used. Accordingly, the proximal minimum gap length $l_{e1}$, which is the distance between the wire guide and the base part, can be kept constant regardless of the rotation angle $\zeta_1$.

Figure 3:
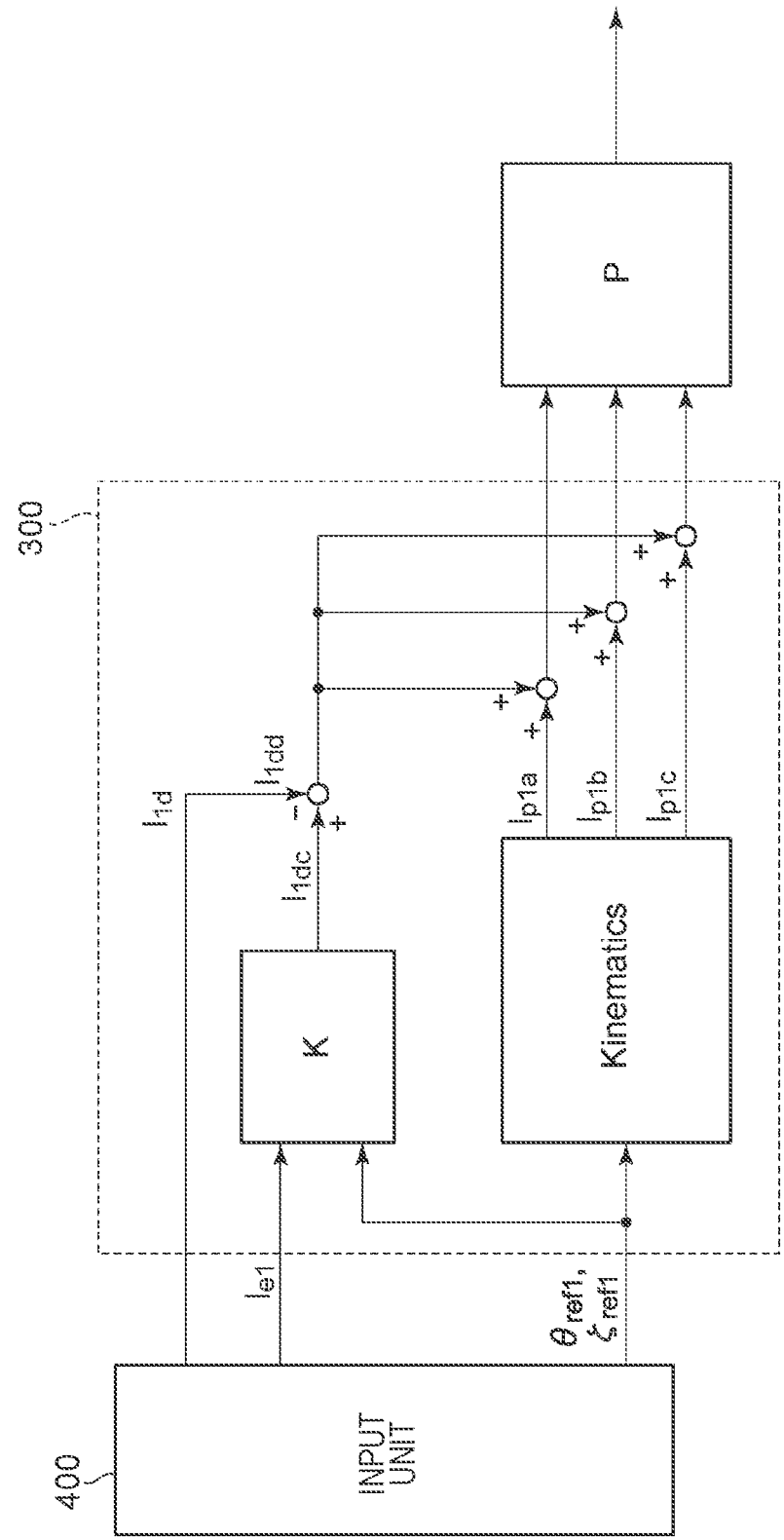
FIG. 3 is a block diagram illustrating a continuum robot control system according to the first embodiment.

FIG. 3 is a block diagram of a control device 300, which is a control unit of the continuum robot 100 according to this embodiment. Here, P represents the continuum robot 100. The control device 300 includes a block K and a block Kinematics. Kinematics is a block that calculates wire driving displacements on the basis of the kinematic model, and corresponds to a first calculation unit. The block K corresponds to a second calculation unit. An input unit 400 inputs the proximal minimum gap length $l_{e1}$ and desired angle vectors $\theta_{ref1}$ and $\zeta_{ref1}$ to the control device 300.

When the desired angle vectors $\theta_{ref1}$ and $\zeta_{ref1}$ are set, the block Kinematics calculates the wire driving displacements $l_{p1a}$, $l_{p1b}$, and $l_{p1c}$. Here, the block K uses the proximal minimum gap length $l_{e1}$ and the desired angle vectors $\theta_{ref1}$ and $\zeta_{ref1}$ as input and outputs the length $l_{1dc}$ of the central axis of the bending section for keeping $l_{e1}$ constant regardless of the rotation angle $\zeta_1$. Then, the difference from the central axis initial length $l_{1d}$ is assumed to be a gap length compensation amount $l_{1dd}$, which is added to each of the wire driving displacements $l_{p1a}$, $l_{p1b}$, and $l_{p1c}$ output from the block Kinematics. Accordingly, the wire driving displacements when the proximal minimum gap length is $l_{e1}$ and the bending and rotation angles are set to $\theta_1$ and $\zeta_1$ respectively are calculated.

Here, for the block K to calculate the length $l_{1dc}$ of the central axis, the central axis initial length $l_{1d}$ in equations (2) and (3) are replaced by $l_{1dc}$, and the equations need to be solved for the central axis length $l_{1dc}$. When the bending angle $\theta_1$ is positive, the following holds.

[Math. 4]

$$l_{1dc} = \frac{(-l_{p1a} + l_{aw} + r\theta_1 + l_{e1}) \pm \sqrt{-(l_{p1a} + l_{aw} + r\theta_1 + l_{e1})^2 - 4(-r\theta_1 l_{p1a} + r\theta_1 l_{aw} - l_{e1}l_{p1a})}}{2} \quad (4)$$

When the bending angle $\theta_1$ is negative, the following holds.

[Math. 5]

$$l_{1dc} = \frac{(-l_{p1a} + l_{aw} - r\theta_1 + l_{e1}) \pm \sqrt{(-l_{p1a} + l_{aw} - r\theta_1 + l_{e1})^2 - 4(r\theta_1 l_{p1a} - r\theta_1 l_{aw} - l_{e1}l_{p1a})}}{2} \quad (5)$$

The difference from the central axis initial length $l_{1d}$ is assumed to be the gap length compensation amount $l_{1dd}$ as follows.

$$l_{1dd} = l_{1dc} - l_{1d} \quad (6)$$

Then, the gap length compensation amount $l_{1dd}$ is added to each of the wire driving displacements $l_{p1a}$, $l_{p1b}$, and $l_{p1c}$ output from the block Kinematics. Accordingly, the wire driving displacements when the proximal minimum gap length is $l_{e1}$ and the bending and rotation angles are set to $\theta_1$ and $\zeta_1$ respectively are calculated.

1.3) Simulation

The results of simulation in which the above-described control system is used to rotate the continuum robot 100 are described. Here, the rotation angle $\zeta_1$ of the continuum robot 100 is changed from 0 degree to 359 degrees in increments of one degree, and the proximal minimum gap length $l_{e1}$, the proximal maximum gap length $l_{eo1}$, and the minimum and maximum gap lengths $l_{gi}$ and $l_{go}$ between the wire guides are calculated. The gap lengths between the wire guides are calculated by using an arc of a circle centered at the point C in the wz plane similarly to the proximal gap lengths. In the simulation, the wire guides are equally spaced and arranged such that the central axis initial length $l_{1d}$ of the bending section is 0.010 m, the number of wire guides is five, the thickness of the wire guides is 0.00075 m, and the distance between the wire guides is 0.00125 m, and the wire driving amounts are calculated such that the proximal minimum gap length $l_{e1}$ is 0.00125 m.

Figure 4A:
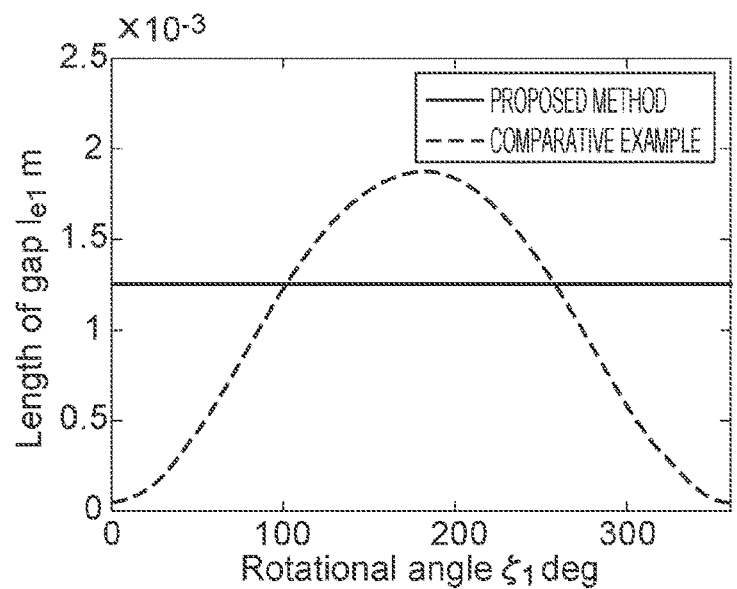
FIG. 4A is a diagram illustrating simulation responses according to the first embodiment.
Figure 4B:
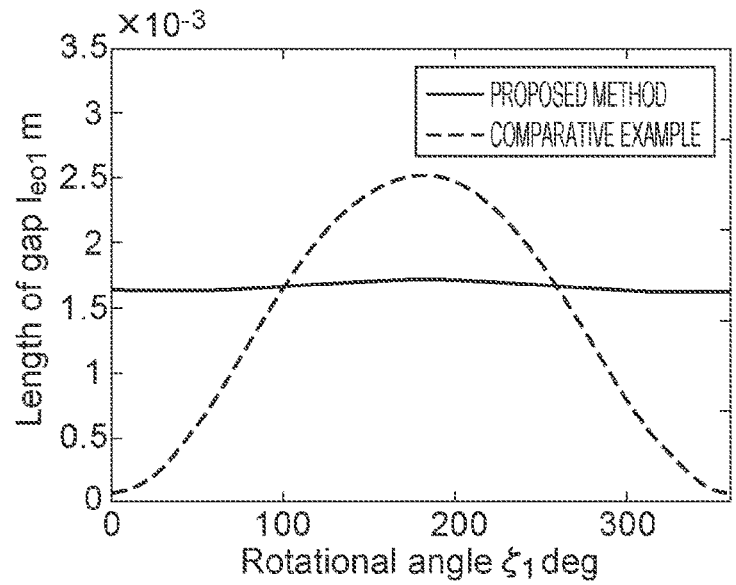
FIG. 4B is a diagram illustrating simulation responses according to the first embodiment.
Figure 4C:
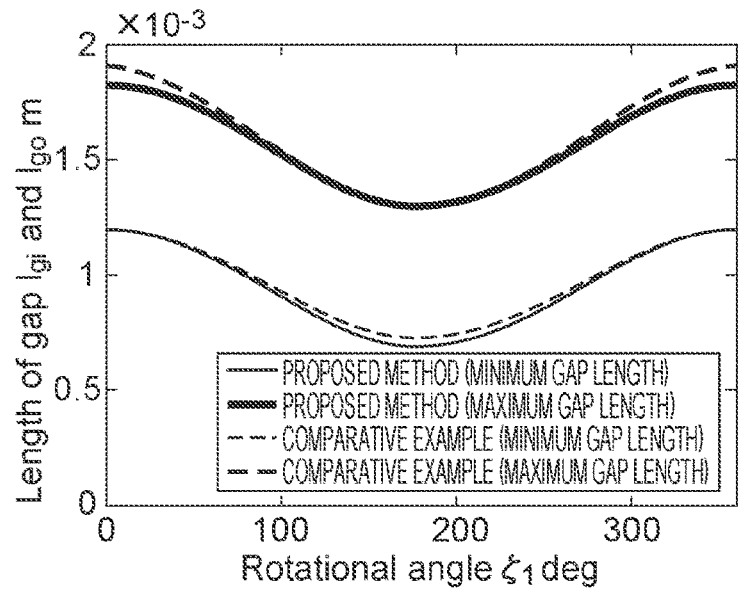
FIG. 4C is a diagram illustrating simulation responses according to the first embodiment.

Simulation responses when the bending angle $\theta_1$ is 55 degrees are illustrated in FIGS. 4A to 4C. Responses obtained by using the control system according to this embodiment (hereinafter referred to as proximal-minimum-gap keeping-constant control) are represented by solid lines, and responses obtained as a result of control in which only equations (1) are used to keep the central axis length constant (hereinafter referred to as central-axis-length keeping-constant control) are represented by dashed lines for a comparison.

FIG. 4A illustrates responses of the proximal minimum gap length $l_{e1}$. In the proximal-minimum-gap keeping-constant control, the proximal minimum gap length $l_{e1}$ is constant regardless of the rotation angle $\zeta_1$. However, in the central-axis-length keeping-constant control, the wire guide 164 is pulled in the base part direction together with a-wire in the direction of a rotation angle of 0 degree, and therefore, the proximal minimum gap length becomes short. It is shown that the proximal minimum gap length becomes long in the direction of a rotation angle of 180 degrees. That is, in the central-axis keeping-constant control, the proximal minimum gap length changes in accordance with the rotation angle $\zeta_1$.

FIG. 4B illustrates responses of the proximal maximum gap length $l_{eo1}$. In the proximal-minimum-gap keeping-constant control, the proximal maximum gap length $l_{eo1}$ is substantially constant regardless of the rotation angle $\zeta_1$. However, in the central-axis-length keeping-constant control, the response is similar to that of the proximal minimum gap length.

In FIG. 4C, responses of the minimum gap length $l_{gi}$ between the wire guides are represented by thin lines, and responses of the maximum gap length $l_{go}$ therebetween are represented by thick lines. It is shown that the range of changes in the minimum gap length between the wire guides by the proximal-minimum-gap keeping-constant control is wider than the range of changes therein by the central-axis-length keeping-constant control but the range of changes in the maximum gap length is narrower than the range of changes by the central-axis-length keeping-constant control.

As indicated by the above-described results, it is found that with the proximal-minimum-gap keeping-constant control proposed in this embodiment, the ranges of changes in the gap lengths between the wire guides are equivalent to those in the central-axis-length keeping-constant control and that the range of changes in the proximal minimum length and that in the maximum gap length due to the rotation angle can be reduced.

Figure 5A:
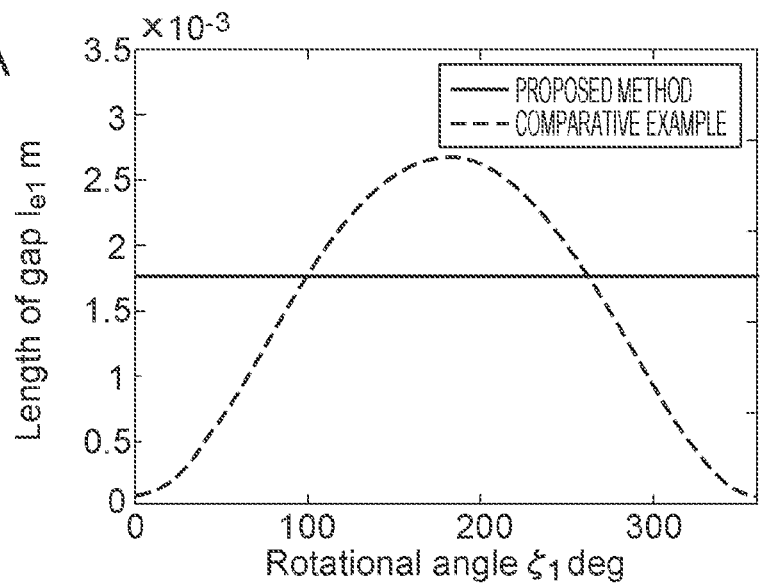
FIG. 5A is another diagram illustrating simulation responses according to the first embodiment.
Figure 5B:
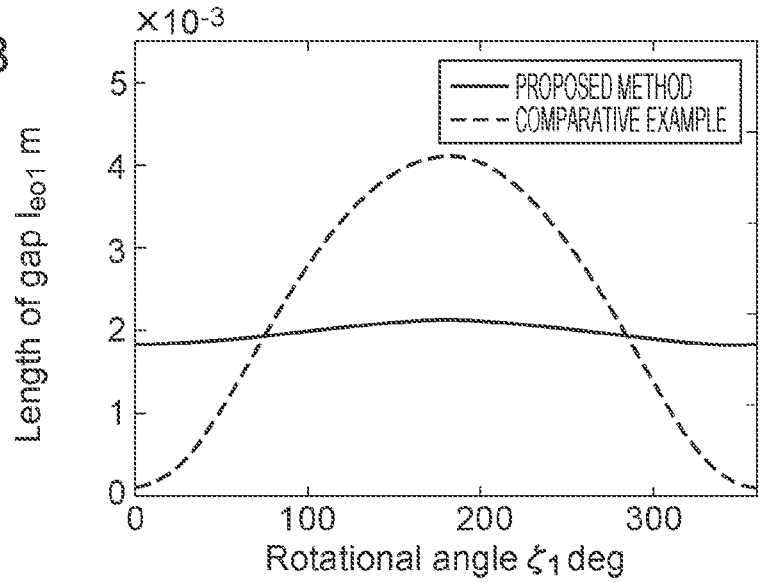
FIG. 5B is another diagram illustrating simulation responses according to the first embodiment.
Figure 5C:
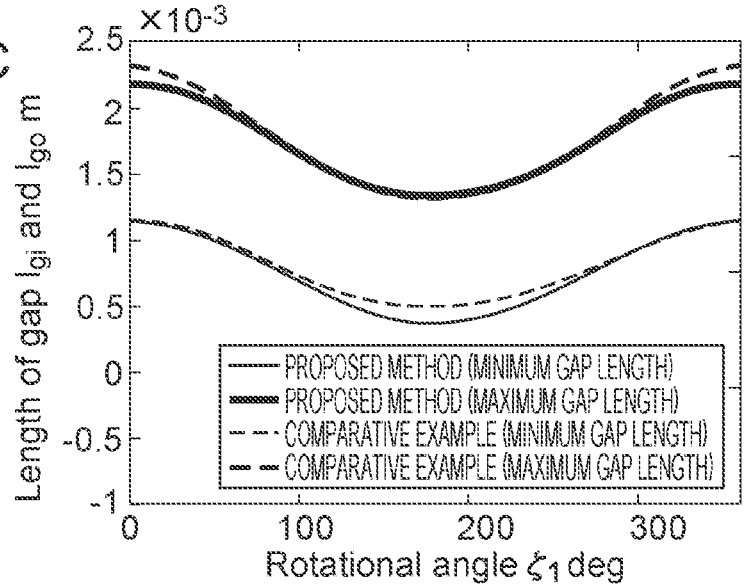
FIG. 5C is another diagram illustrating simulation responses according to the first embodiment.

Simulation responses when the bending angle $\theta_1$ is 90 degrees are illustrated in FIGS. 5A to 5C. When the central axis initial length $l_{1d}$ is 0.010 m, in the case where the bending angle $\theta_1$ is 90 degrees, the proximal minimum gap length is negative in the central-axis keeping-constant control, and the limit of the bending angle of the bending section is exceeded. Therefore, the central axis initial length $l_{d1}$ is assumed to be 0.0108 m and a calculation is made. As found from the results illustrated in FIGS. 5A to 5C, tendencies similar to those in FIG. 4 are also shown under the above-described conditions. Accordingly, with the proximal-minimum-gap keeping-constant control, the ranges of changes in the gap lengths between the wire guides are equivalent to those in the central-axis-length keeping-constant control, and the range of changes in the proximal minimum length and that in the maximum gap length due to the rotation angle can be reduced.

According to this embodiment, the accuracy of control of the continuum robot can be increased.

Second Embodiment

In the first embodiment, the control system for keeping the proximal minimum gap length $l_{e1}$ constant regardless of the rotation angle $\zeta_1$ has been described. Although the kinematics assume that the wires do not deform in the longitudinal direction, the wires actually expand and contract due to form control, and the performance of gap length compensation decreases. Specifically, when the gap length compensation amount is negative at the time of wire compression, the wire guide at the proximal end may come into contact with the base part. In this embodiment, a regulating gain is introduced into the control system as a measure for such expansion and contraction of the wires.

2.1) Modeling

The continuum robot 100 is common to that described in the first embodiment, and therefore, a description thereof is omitted here.

2.2) Control System Design

Figure 6:
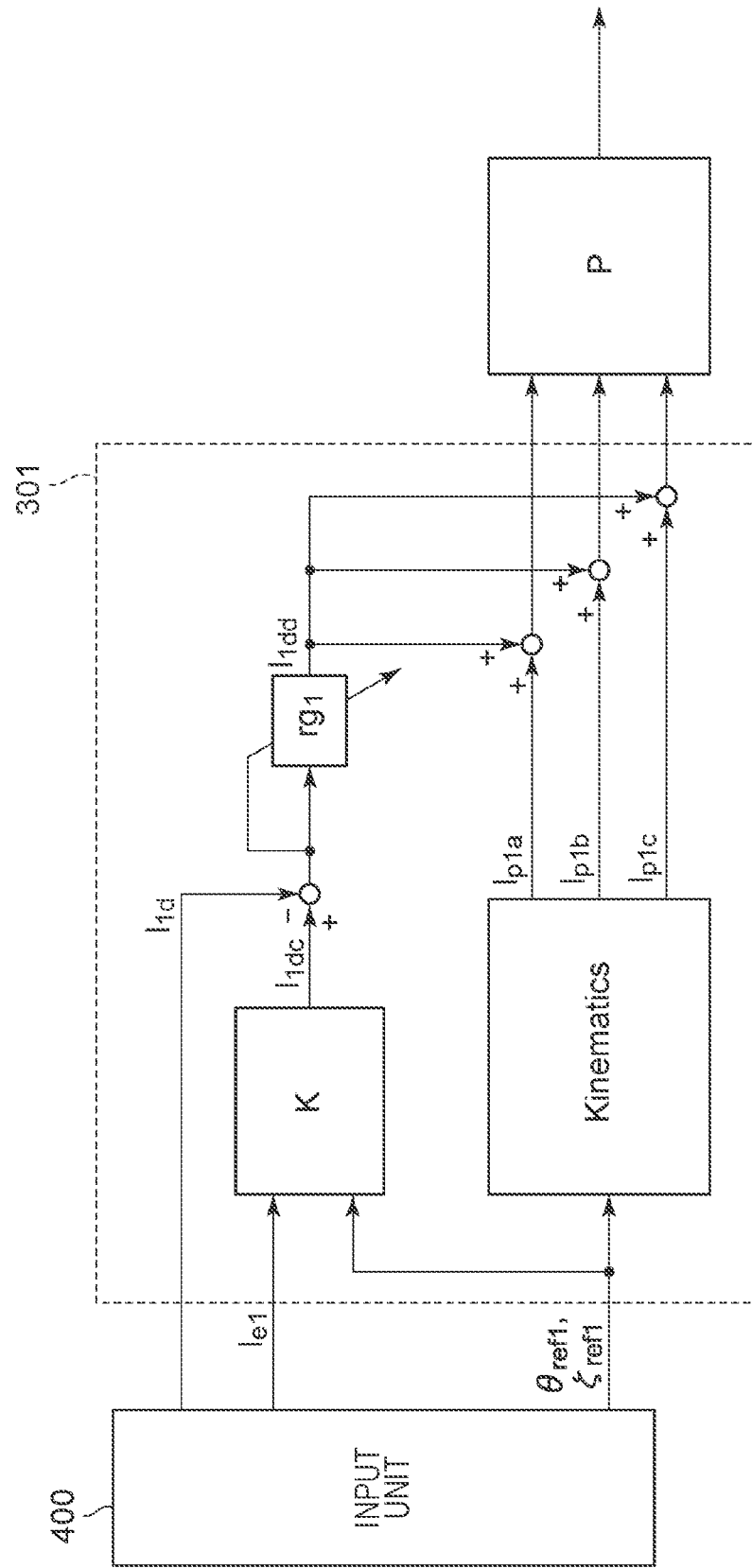
FIG. 6 is a block diagram illustrating a continuum robot control system according to a second embodiment.

FIG. 6 is a block diagram illustrating a control device 301 according to this embodiment. The control device 301 is different from the control device 300 in that the control device 301 includes a block $rg_1$ that multiples the difference $l_{sb1}$ between the central axis length $l_{1dc}$ and the central axis initial length $l_{1d}$ by a regulating gain $r_{g1}$. With the block $r_{g1}$, the gap length compensation amount $l_{1dd}$ becomes as follows.

$$l_{1dd} = rg_1(l_{1dc} - l_{1d}) = rg_1 l_{sb1} \quad (7)$$

Here, the regulating gain $rg_1$ may be changed in accordance with the difference $l_{sb1}$. For example, the regulating gain $r_{g1}$ may be switched as follows depending on whether the difference $l_{sb1}$ is positive or negative.

[Math. 6]

$$rg_1 = rg_{1p}(l_{sb1} \geq 0)$$

$$rg_1 = rg_{1m}(l_{sb1} < 0)$$

$$rg_{1m} < rg_{1p} \quad (8)$$

Accordingly, the control system can be regulated in response to actual expansion and contraction of the wire lengths.

Third Embodiment

In the second embodiment, the method for reducing an error in the gap length when the wires expand or contract has been described. However, the expansion-contraction amounts of the wires in the continuum robot nonlinearly change in accordance with the rotation angle $\zeta_1$, and therefore, it is not possible to compensate the gap length with high accuracy with the method of switching the regulating gain in accordance with whether the difference $l_{sb1}$ is positive or negative as expressed by equations (8). Accordingly, in this embodiment, a static model of the continuum robot is derived, and this model is used to calculate the wire expansion-contraction amounts.

(Modeling)

The definitions of symbols used in the description of this embodiment are described below.
E: the Young's modulus of the wires
A: the cross-sectional area of the wires
I: the cross-sectional secondary moment of the wires
$L_0$: the total length of a-, b-, and c-wires Note that this embodiment assumes that the wire driving amount $l_{p1b}$, wire expansion-contraction amounts $\Delta l_a$, $\Delta l_b$, and $\Delta l_c$, and wire tensions $f_a$, $f_b$, and $f_c$ are positive in the distal end direction and that moments $M_a$, $M_b$, and $M_c$ are positive in the clockwise direction.

In this embodiment, expansion and contraction of the wires are taken into consideration, and a static model is considered under assumptions 5 to 10 described below in addition to assumption 1, assumption 2, and assumption 4 described in the first embodiment.

[5]: Forces and moments acting between the wire guides and the wires are not taken into consideration.
[6]: In a force acting between a wire and the distal wire guide, only a component in the longitudinal direction of the wire is taken into consideration, and a component in the radial direction thereof is not taken into consideration.
[7]: The expansion-contraction amount of a wire is proportional to a tension acting on the wire.
[8]: The bending moment of a wire is proportional to the deflection angle.
[9]: The wires have the same tensile rigidity and the same flexural rigidity.
[10]: The wires have the same Young's modulus, the same cross-sectional area, and the same cross-sectional secondary moment.

From an equation expressing the balance between a force and a moment acting on the distal wire guide 160 and each wire, the wire expansion-contraction amounts $\Delta l_a$, $\Delta l_b$, and $\Delta l_c$ of a-, b-, and c-wires are derived. In this embodiment, a $z_2$ axis is set on an extension line of the central axis of the bending section, and an $x_2$ axis is set in a direction straight to the $z_2$ axis on a $z_1 w_1$ plane. Then, $y_2$ is set as a coordinate axis of a right-hand system straight to $z_2$ and $x_2$. From assumption 4, assumption 5, and assumption 6 described above, the tensions $f_a$, $f_b$, and $f_c$ of a-, b-, and c-wires in the longitudinal direction and the moments $M_a$, $M_b$, and $M_c$ around the $y_2$ axis caused by the bending wires act on the distal wire guide. The balance among forces in the $Z_2$ direction of the distal wire guide 160 is expressed by equation (9) below using forces $f_{1a}$, $f_{1b}$, and $f_{1c}$.

[Math. 7]
$$f_a + f_b + f_c = 0 \tag{9}$$

The balance among the bending moments $M_a$, $M_b$, and $M_c$ around the $Y_2$ axis and moments produced by the forces $f_a$, $f_b$, and $f_c$ from the wires is expressed by equation (10) below.

[Math. 8]
$$r\left\{f_a\sin\left(-\zeta_1-\frac{\pi}{2}\right)+f_b\sin\left(-\zeta_1+\frac{\pi}{6}\right)+f_c\sin\left(-\zeta_1+\frac{5\pi}{6}\right)\right\}- \tag{10}$$
$$M_a - M_b - M_c = 0$$

Further, moments are produced by the forces $f_a$, $f_b$, and $f_c$ around the $X_2$ axis, and therefore, the balance is expressed by equation (11) below.

[Math. 9]
$$r\left\{f_a\sin(-\zeta_1)+f_b\sin\left(-\zeta_1+\frac{2\pi}{3}\right)+f_c\sin\left(-\zeta_1+\frac{4\pi}{3}\right)\right\}=0 \tag{11}$$

Next, equation (9), equation (10), and equation (11) are transformed to calculate relationships between the central axis length and the wire expansion-contraction amounts.

From assumption 7, assumption 8, and assumption 9 described above, the forces $f_a$, $f_b$, and $f_c$ and the moments $M_a$, $M_b$, and $M_c$ are respectively expressed by equations (12) and equations (13) below using the expansion-contraction amounts $\Delta l_{1a}$, $\Delta l_{1b}$, and $\Delta l_{1c}$ and the bending angle $\theta_1$.

[Math. 10]
$$f_a = -k_e \Delta l_{1a} \tag{12}$$
$$f_b = -k_e \Delta l_{1b}$$
$$f_c = -k_e \Delta l_{1c}$$
$$M_a = -k_m \frac{\theta_1}{l_{1a}} \tag{13}$$
$$M_b = -k_m \frac{\theta_1}{l_{1b}}$$
$$M_c = -k_m \frac{\theta_1}{l_{1c}}$$

Note that in equations (12) and equations (13), the constant $k_e$ and the constant $k_m$ respectively represent the tensile rigidity and the flexural rigidity of the wires. The constant $k_e$ and the constant $k_m$ can be respectively expressed by equation (14) and equation (15) from assumption 10 described above using the total wire length $L_0$, the cross-sectional area A of the wires, the cross-sectional secondary moment I, and the Young's modulus E.

[Math. 11]
$$k_e = \frac{AE}{L_0} \tag{14}$$
$$k_m = EI \tag{15}$$

When it is assumed that the expansion-contraction amounts $\Delta l_{1a}$, $\Delta l_{1b}$, and $\Delta l_{1c}$ are sufficiently smaller than the central axis length, the lengths $l_{1a}$, $l_{1b}$ and $l_{1c}$ of a-, b-, and c-wires in the bending section can be expressed by equations (16) below.

[Math. 12]

$$l_{1a} = -\frac{r_s}{\sqrt{3}}\cos(\zeta_1 - \xi_1)\theta_1 + l_{1dc}$$

$$l_{1b} = -\frac{r_s}{\sqrt{3}}\cos\left(\frac{2\pi}{3} - \zeta_1 + \xi_1\right)\theta_1 + l_{1dc} \quad (16)$$

$$l_{1c} = -\frac{r_s}{\sqrt{3}}\cos\left(\frac{4\pi}{3} - \zeta_1 + \xi_1\right)\theta_1 + l_{1dc}$$

When the forces $f_a$, $f_b$, and $f_c$ and the moments $M_a$, $M_b$, and $M_e$ are eliminated from equations (9) to (13) and equations (16) and a vector $\Delta l_1$, a vector $m_1$, a matrix A, and a matrix $K_e$ are respectively defined by equation (17), equation (18), equation (19), and equation (20), the wire expansion-contraction amount $\Delta l_1$ is expressed by equation (21).

[Math. 13]

$$\Delta l_1 = [\Delta l_{1a} \quad \Delta l_{1b} \quad \Delta l_{1c}]^T \quad (17)$$

$$m_1 = \left[0 \quad -k_m\theta_1 \left\{ \begin{array}{c} \dfrac{1}{-\dfrac{r_s}{\sqrt{3}}\cos(\zeta_1 - \xi_1)\theta_1 + l_{1dc}} + \\ \dfrac{1}{-\dfrac{r_s}{\sqrt{3}}\cos\left(\dfrac{2\pi}{3} - \zeta_1 + \xi_1\right)\theta_1 + l_{1dc}} + \\ \dfrac{1}{-\dfrac{r_s}{\sqrt{3}}\cos\left(\dfrac{4\pi}{3} - \zeta_1 + \xi_1\right)\theta_1 + l_{1dc}} \end{array} \right\}^T \quad 0\right] \quad (18)$$

$$A = \begin{bmatrix} 1 & 1 & 1 \\ r\sin\left(-\zeta_1 - \dfrac{\pi}{2}\right) & r\sin\left(-\zeta_1 + \dfrac{\pi}{6}\right) & r\sin\left(-\zeta_1 + \dfrac{5\pi}{6}\right) \\ r\sin(-\zeta_1) & r\sin\left(-\zeta_1 + \dfrac{2\pi}{3}\right) & r\sin\left(-\zeta_1 + \dfrac{4\pi}{3}\right) \end{bmatrix} \quad (19)$$

$$K_e = \begin{bmatrix} k_e & 0 & 0 \\ 0 & k_e & 0 \\ 0 & 0 & k_e \end{bmatrix} \quad (20)$$

$$\Delta l_1 = (AK_e)^{-1} m_1 \quad (21)$$

(Control System Design)

Figure 7:
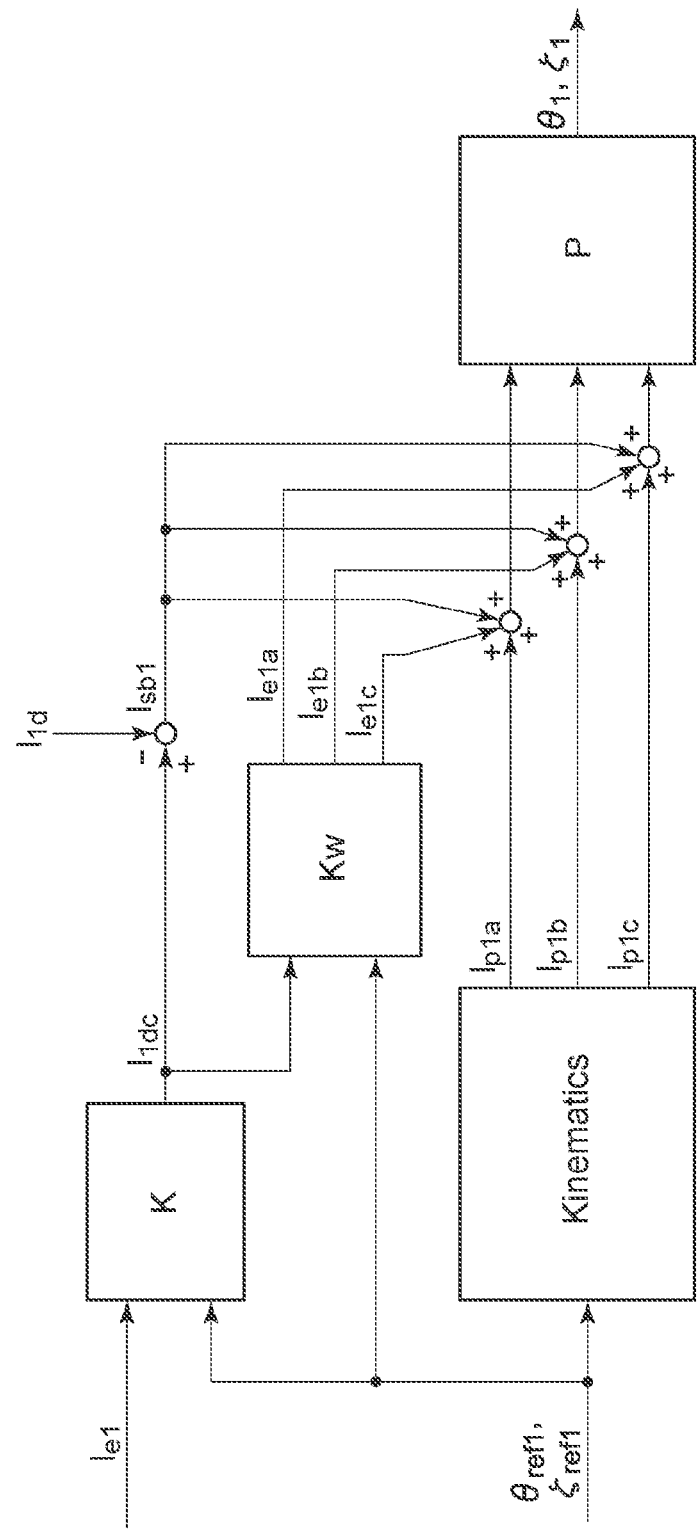
FIG. 7 is a block diagram illustrating a continuum robot control system according to a third embodiment.

FIG. 7 is a block diagram of a control device 303 according to this embodiment for compensating for expansion and contraction of the wires. Note that the block Kinematics and the block K are common to those described in the first embodiment, and therefore, descriptions thereof are omitted here. A block $K_w$ uses the desired angle vectors $\theta_{ref1}$ and $\zeta_{ref1}$ and the central axis length $l_{1dc}$ as input, calculates the expansion-contraction amounts $\Delta l_{1a}$, $\Delta l_{1b}$, and $\Delta l_{1c}$ of the respective wires using equation (21), and outputs the results of calculation as wire expansion-contraction compensation amounts $l_{e1a}$, $l_{e1b}$, and $l_{e1c}$ expressed by equations (22).

[Math. 14]

$$l_{e1a} = -\Delta l_{1a}$$

$$l_{e1b} = -\Delta l_{1b}$$

$$l_{e1c} = -\Delta l_{1c} \quad (22)$$

The wire expansion-contraction compensation amounts $l_{e1a}$, $l_{e1b}$, and $l_{e1c}$ as well as the difference $l_{sb1}$ are added to the wire driving displacements $l_{p1a}$, $l_{p1b}$, and $l_{p1c}$ respectively. Accordingly, even in a case where the wires expand or contract, the wire driving displacements when the proximal minimum gap length is $l_{e1}$ and the bending and rotation angles are set to $\theta_1$ and $\zeta_1$ respectively are calculated.

(Simulation)

The results of simulation in which the above-described control system is used to rotate the continuum robot 100 are described. In this embodiment, the proximal minimum gap length $l_{e1}$ and the bending angle $\theta_1$ when the rotation angle $\zeta_1$ of the continuum robot 100 is changed from 0 degree to 359 degrees in increments of one degree are calculated. In the simulation, the central axis initial length $l_{1d}$ in the bending section is set to 0.010 m, the total length $L_0$ of the wires is set to 1.0 m, and the wire driving amounts are calculated such that the proximal minimum gap length $l_{e1}$ is 0.00125 m.

Figure 8A:
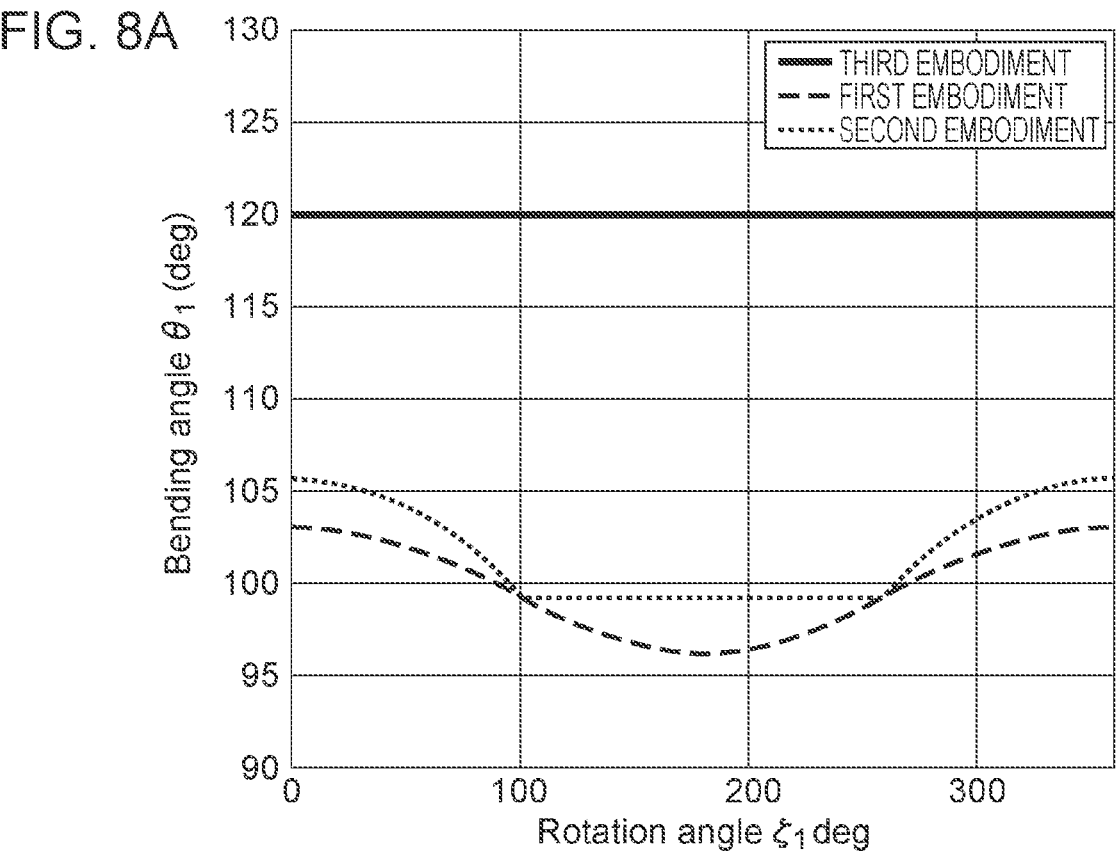
FIG. 8A is a diagram illustrating simulation responses according to the third embodiment.
Figure 8B:
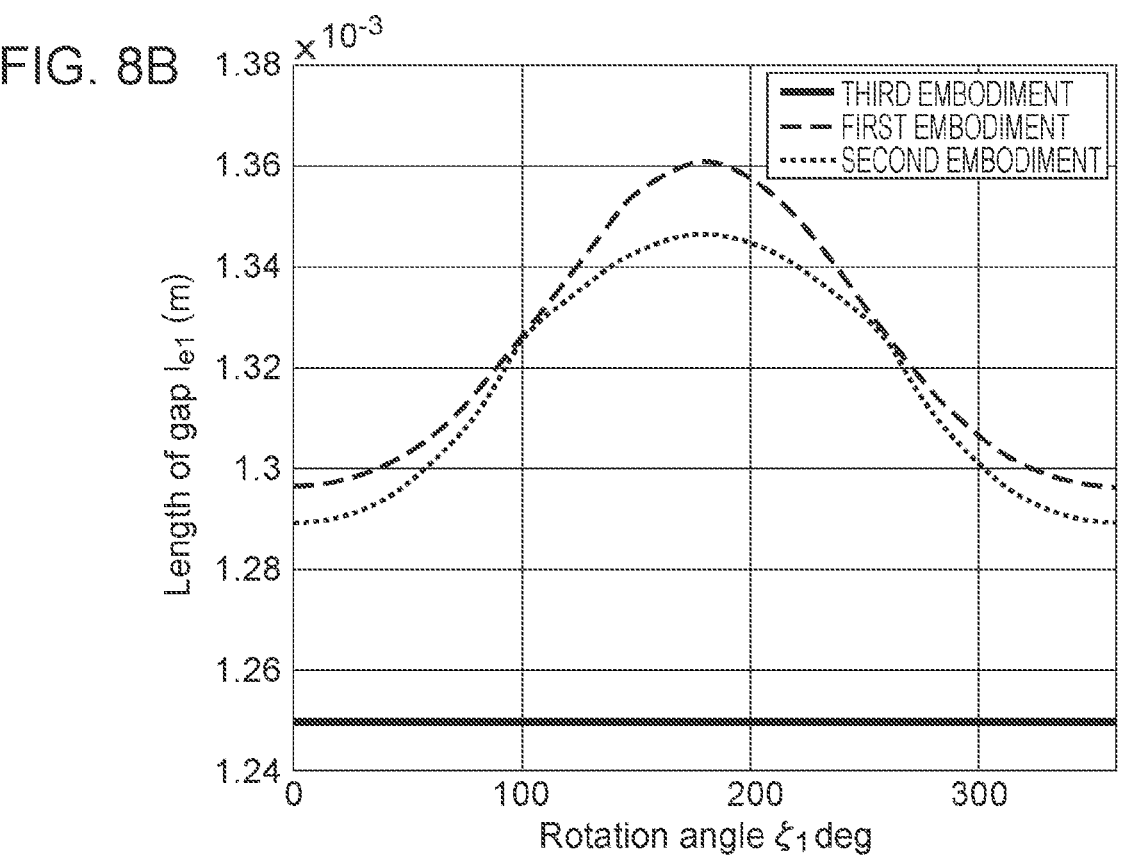
FIG. 8B is a diagram illustrating simulation responses according to the third embodiment.

Simulation responses when the desired bending angle $\theta_{ref1}$ is 120 degrees are illustrated in FIGS. 8A and 8B. Responses obtained by using the control system according to this embodiment are represented by solid lines. Responses obtained as a result of the control in the first embodiment in which expansion or contraction of the wires is not taken into consideration are represented by dashed lines, and responses obtained as a result of the control in the second embodiment as expressed by equations (8) are represented by dotted lines for a comparison.

FIG. 8A illustrates responses of the bending angle $\theta_1$. With the control of this embodiment, the bending angle $\theta_1$ matches the rotation angle $\zeta_1$ regardless of the rotation angle $\zeta_1$. However, with the control of the first embodiment, the bending angle $\theta_1$ becomes smaller than the desired bending angle $\theta_{ref1}$ due to expansion and contraction of the wires. With the control of the second embodiment, the control error is reduced but it is not possible to completely compensate for the error.

FIG. 8B illustrates responses of the proximal minimum gap length $l_{e1}$. With the control of this embodiment, the proximal minimum gap length $l_{e1}$ is constant regardless of the rotation angle $\zeta_1$. However, with the control of the first embodiment and that of the second embodiment, the gap length is affected by the error in the bending angle and increases, and further, the length changes in accordance with the rotation angle $\zeta_1$.

As indicated by the above-described results, with the control system of this embodiment in which the expansion-contraction amounts of the wires are calculated using a static model, changes in the proximal minimum length and an error in the bending angle can be reduced.

Fourth Embodiment

In the above-described embodiments, an example of a continuum robot having one bending section has been described. In this embodiment, a continuum robot having a plurality of bending sections is a target.

3.1) Modeling

Figure 9:
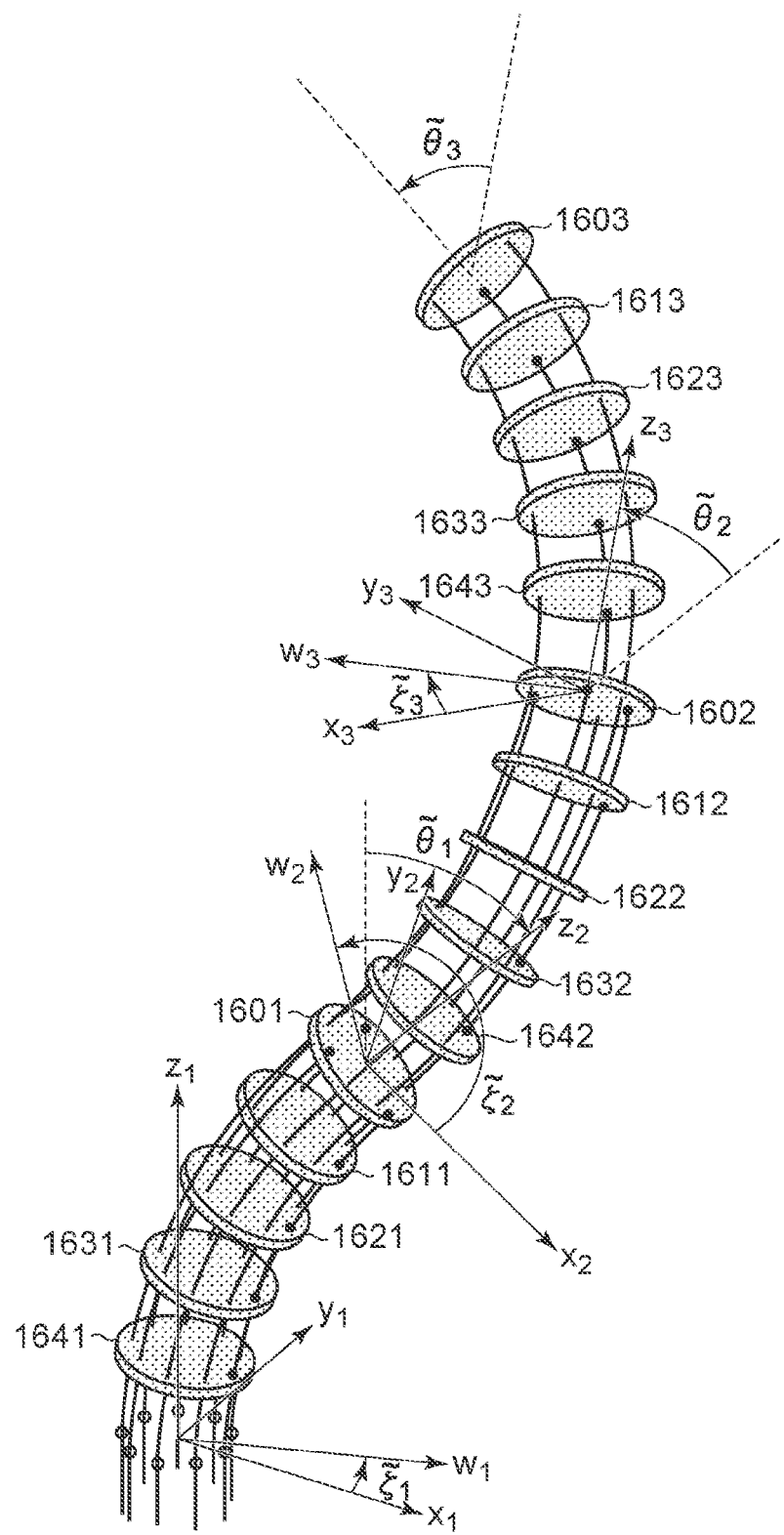
FIG. 9 is a diagram illustrating a kinematic model of a continuum robot according to a fourth embodiment.

FIG. 9 is a schematic diagram of a continuum robot having n bending sections and also illustrates coordinate systems. FIG. 9 illustrates only a part formed of three contiguous bending sections among the n bending sections. As in the continuum robot illustrated in FIG. 1, each bending section is configured such that its posture is controlled by three wires and one wire among the three wires is fixed to each wire guide of the bending section. In the configuration illustrated in FIG. 9, wire guides 1602 and 1603, which are distal guides of the respective bending sections, and the $x_1 y_1$ plane are the reference planes for the respective bending sections.

The distal end and wire guide of the n-th bending section also serve as a wire guide of the more distal bending section. In the present invention, as the relative coordinate system of the n-th bending section, a $z_n$ axis is set on an extension line of the central axis of the n−1-th bending section, and an xd axis is set in a direction straight to the $z_n$ axis on a $z_{n-1} w_{n-1}$ plane. Then, $y_n$ is set as a coordinate axis of a right-hand system straight to $z_n$ and $x_n$. The bending angle and the rotation angle in the relative coordinate system of the n-th bending section are respectively represented as follows.

[Math. 15]

$$\hat{\theta}_n, \hat{\xi}_n$$

To set the bending angle and the rotation angle of the distal end below

[Math. 16]

$$\hat{\theta}_n, \hat{\xi}_n$$

candidates for the driving displacements of a-, b-, and c-wires in the relative coordinate system $x_n y_n z_n$, namely,

[Math. 17]

$$\tilde{l}_{pna}, \tilde{l}_{pnb}, \tilde{l}_{pnc}$$

are expressed as follows.

[Math. 18]

$$\tilde{l}_{pna} = -\frac{r_s}{\sqrt{3}} \cos(\xi_n - \xi_n) \tilde{\theta}_n \quad (9)$$

$$\tilde{l}_{pnb} = -\frac{r_s}{\sqrt{3}} \cos\left(\frac{2\pi}{3} - \xi_n + \xi_n\right) \tilde{\theta}_n$$

$$\tilde{l}_{pnc} = -\frac{r_s}{\sqrt{3}} \cos\left(\frac{4\pi}{3} - \xi_n + \xi_n\right) \tilde{\theta}_n$$

As in the first embodiment, when the bending angle, namely,

[Math. 19]

$$\hat{\theta}_n$$

is positive, the proximal minimum gap length $l_{en}$ of the n-th bending section is expressed as follows.

[Math. 20]

$$l_{en} = (l_{nd} - r\tilde{\theta}_n) \frac{l_{nd} + \tilde{l}_{pna} - l_{aw}}{l_{nd} + \tilde{l}_{pna}} \quad (10)$$

When the bending angle, namely,

[Math. 21]

$$\hat{\theta}_n$$

is negative, the proximal minimum gap length $l_{en}$ is expressed as follows.

[Math. 22]

$$l_{en} = (l_{nd} + r\tilde{\theta}_n) \frac{l_{nd} + \tilde{l}_{pna} - l_{aw}}{l_{nd} + \tilde{l}_{pna}} \quad (11)$$

3.2) Control System Design

Figure 10:
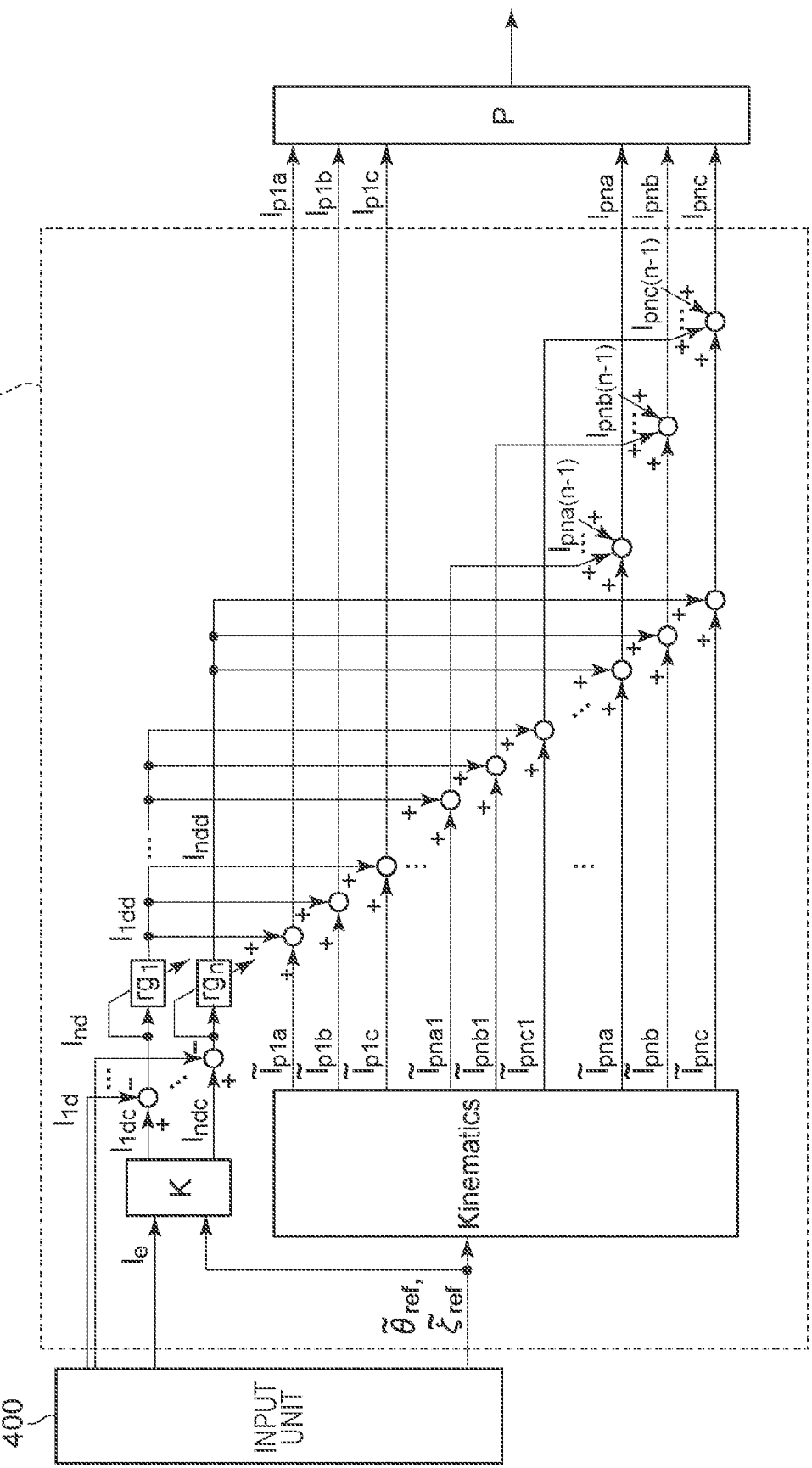
FIG. 10 is a block diagram illustrating a continuum robot control system according to the fourth embodiment.

FIG. 10 is a block diagram of a control system for keeping the proximal minimum gap length $l_{en}$ constant regardless of the rotation angle below.

[Math. 23]

$$\hat{\xi}_n$$

Desired angle vectors, namely,

[Math. 24]

$$\hat{\theta}_{ref}, \hat{\xi}_{ref}$$

are expressed as follows.

[Math. 25]

$$\hat{\theta}_{ref} = [\hat{\theta}_1 \hat{\theta}_2 \ldots \hat{\theta}_n]^T, \hat{\xi}_{ref} = [\hat{\xi}_1 \hat{\xi}_2 \ldots \hat{\eta}_n]^T, \quad (12)$$

Then, the block Kinematics uses equations (16) to calculate the wire driving displacements below.

[Math. 26]

$$\tilde{l}_{pna}, \tilde{l}_{pnb}, \tilde{l}_{pnc}$$

As in the control system described in the first embodiment, the block K uses the proximal minimum gap length $l_e = [l_{e1} l_{e2} \ldots l_{en}]$ as input and outputs the length $l_{ndc}$ (n=1, ..., e) of the central axis of the bending section for keeping the length $l_e$ constant regardless of the rotation angle in the corresponding relative coordinate system below.

[Math. 27]

$$\hat{\xi}_n$$

To calculate the length $l_{ndc}$ (n=1, ..., e) of the central axis, the central axis initial length $l_{nd}$ in equations (10) and (11) needs to be replaced by $l_{ndc}$, and the equations need to be solved for the central axis length $l_{ndc}$. When the bending angle, namely,

[Math. 28]

$$\hat{\theta}_n$$

is positive, the following holds.

[Math. 29]

$$l_{ndc} = \frac{(-\tilde{l}_{pna} + l_{aw} + r\tilde{\theta}_n + l_{en}) \pm \sqrt{(-\tilde{l}_{pna} + l_{aw} + r\tilde{\theta}_n + l_{en})^2 - 4(-r\tilde{\theta}_n \tilde{l}_{pna} + r\tilde{\theta}_n l_{aw} - l_{en}\tilde{l}_{pna})}}{2} \quad (13)$$

When the bending angle, namely,

[Math. 30]

$$\hat{\theta}_n$$

is negative, the following holds.

[Math. 31]

$$l_{ndc} = \frac{(-\tilde{l}_{pna} + l_{aw} - r\tilde{\theta}_n + l_{en}) \pm \sqrt{(-\tilde{l}_{pna} + l_{aw} - r\tilde{\theta}_n + l_{en})^2 - 4(r\tilde{\theta}_n \tilde{l}_{pna} - r\tilde{\theta}_n l_{aw} - l_{en}\tilde{l}_{pna})}}{2} \quad (14)$$

Then, the difference from the central axis initial length $l_{nd}$ is multiplied by a regulating gain as in the second embodiment to calculate a gap length compensation amount $l_{ndd}$ as follows.

$$l_{ndd} = rg_n(l_{ndc} - l_{nd}) \tag{15}$$

This is added to the wire driving displacements, namely,
[Math. 32]

$$\tilde{l}_{pna}, \tilde{l}_{pnb}, \tilde{l}_{pnc}$$

output from the block Kinematics. Accordingly, the wire driving displacements when the proximal minimum gap length is $l_{en}$ and the bending and rotation angles are $\theta_n$ and $\zeta_n$ respectively in the n-th relative coordinate system are calculated.

Next, wire driving displacements $l_{pna}$, $l_{pnb}$, and $l_{pnc}$ in the n-th bending section necessary as control input for actuators are calculated. First, the symbols of the wire driving displacements in the n-th relative coordinate system are defined as follows.
[Math. 33]

$$\tilde{l}_{pnam}, \tilde{l}_{pnbm}, \tilde{l}_{pncm}$$

: the driving displacements of a-, b-, and c-wires in the m-th bending section connected to the distal end of the n-th bending section.

These are expressed as follows.

[Math. 34]

$$\tilde{l}_{pnam} = -\frac{r_s}{\sqrt{3}} \cos(\zeta_m - \xi_n)\theta_m$$

$$\tilde{l}_{pnbm} = -\frac{r_s}{\sqrt{3}} \cos\left(\frac{2\pi}{3} - \zeta_m + \xi_n\right)\theta_m \tag{16}$$

$$\tilde{l}_{pncm} = -\frac{r_s}{\sqrt{3}} \cos\left(\frac{4\pi}{3} - \zeta_m + \xi_n\right)\theta_m$$

When these are used, each of the wire driving displacements $l_{pna}$, $l_{pnb}$, and $l_{pnc}$ is the sum of the wire driving displacements in the relative coordinate systems of the first to n-th sections as follows.

[Math. 35]

$$l_{pna} = \tilde{l}_{pna} + l_{ndd} + \sum_{m=1}^{n-1}(\tilde{l}_{pnam} + l_{mdd}) \tag{17}$$

$$l_{pnb} = \tilde{l}_{pnb} + l_{ndd} + \sum_{m=1}^{n-1}(\tilde{l}_{pnbm} + l_{mdd})$$

$$l_{pnc} = \tilde{l}_{pnc} + l_{ndd} + \sum_{m=1}^{n-1}(\tilde{l}_{pncm} + l_{mdd})$$

According to this embodiment, the minimum gap length between a wire guide 164n in the n-th bending section nearest to the proximal side and a distal wire guide 160(n+1) in the adjacent bending section can also be kept constant. As a result, the accuracy of control of the continuum robot can be increased further than in the related art.

Fifth Embodiment

In the fourth embodiment, for a continuum robot having a plurality of bending sections, a relative coordinate system is introduced to each bending section, and kinematics are derived and a control system is designed. However, in a case of control for causing the angle of the most distal bending section to follow a route set in an absolute coordinate system, control based on the absolute coordinate system is simple. Accordingly, in this embodiment, control using an absolute coordinate system is a target.

4.1) Modeling

The continuum robot 100 is common to that described in the fourth embodiment, and therefore, a description thereof is omitted here.

4.2) Coordinate Transformation

First, a procedure for calculating the bending angle $\theta_n$ and the rotation angle $\zeta_n$ in an absolute coordinate system from relative angles is described. In the relative coordinate system of the n-th bending section, on an extension line of the bending form, from the distal end, namely,
[Math. 36]

$$(\tilde{x}_{tn}, \tilde{y}_{tn}, \tilde{z}_{tn})$$

a point at a distance of 1 is set as follows.
[Math. 37]

$$(\tilde{x}_{ttn}, \tilde{y}_{ttn}, \tilde{z}_{ttn})$$

Then, its coordinates are expressed as follows.

[Math. 38]

$$\begin{bmatrix} \tilde{X}_{ttn} \\ \tilde{Y}_{ttn} \\ \tilde{Z}_{ttn} \end{bmatrix} = \begin{bmatrix} \tilde{X}_{tn} \\ \tilde{Y}_{tn} \\ \tilde{Z}_{tn} \end{bmatrix} + \begin{bmatrix} \cos\zeta\sin\theta \\ \sin\zeta\sin\theta \\ \cos\theta \end{bmatrix} \tag{18}$$

A position $(x_{ttn}, y_{ttn}, z_{ttn})$ in the absolute coordinate system is expressed as follows by using rotation transformation matrices.

[Math. 39]

$$\begin{bmatrix} X_{ttn} \\ Y_{ttn} \\ Z_{ttn} \end{bmatrix} = \begin{bmatrix} X_{tn} \\ Y_{tn} \\ Z_{tn} \end{bmatrix} + \sum_{m=2}^{n-1}\prod_{k=1}^{m-1} R_z(\zeta_k + \xi_k)R_y(\theta_k) \begin{bmatrix} \tilde{X}_{tm} \\ \tilde{Y}_{tm} \\ \tilde{Z}_{tm} \end{bmatrix} + \prod_{k=1}^{n} R_z(\zeta_n + \xi_n)R_y(\theta_n) \begin{bmatrix} \tilde{X}_{ttn} \\ \tilde{Y}_{ttn} \\ \tilde{Z}_{ttn} \end{bmatrix} \tag{19}$$

Here, $R_z(\theta)$ and $R_y(\theta)$ are rotation matrices about the z axis and the y axis respectively and expressed as follows.

[Math. 40]

$$R_z(\theta) = \begin{bmatrix} \cos\theta & -\sin\theta & 0 \\ \sin\theta & \cos\theta & 0 \\ 0 & 0 & 1 \end{bmatrix},$$

$$R_y(\theta) = \begin{bmatrix} \cos\theta & 0 & \sin\theta \\ 0 & 1 & 0 \\ -\sin\theta & 0 & \cos\theta \end{bmatrix}$$

These are used to define a unit vector $e_{zn}$ as follows.

$$e_{zn} = (x_{ttn} - x_{tn}, y_{ttn} - y_{tn}, z_{ttn} - z_{tn}) \tag{20}$$

The unit vector $e_{zn}$ represents the direction of the distal end of the n-th bending section in the absolute coordinate system, the angle from the z axis is the bending angle $\theta_n$, and the angle, of the unit vector $e_{zn}$ projected onto the xy plane, from the x axis is the rotation angle $\zeta_n$. To calculate relative angles from the absolute angles, the coordinate axis $z_{n+1}$ of the relative coordinate system for the n+1-th bending section is set in the direction of the unit vector $e_{zn}$, and the $x_{n+1}$ axis is set in a direction straight to the $z_{n+1}$ axis on the $w_n z_n$ plane of the relative coordinate system of the n-th bending section. From a right-hand system, the relative coordinate system of the n+1-th bending section is defined, and therefore, the relative angles are calculated from relationships between the coordinate axes and the unit vector $e_{zn+1}$. In the first bending section, the relative angles are equal to the absolute angles. When the above-described calculations are repeated from the proximal end, the relative angles in every bending section can be calculated.

4.3) Control System Design

When the absolute coordinate system is used, in the central-axis keeping-constant control, the driving displacements $l_{pna0}$, $l_{pnb0}$, and $l_{pnc0}$ of the wires in the n-th bending section, which serve as control input to actuators, can be directly calculated as follows.

[Math. 41]

$$l_{pna0} = -\frac{r_s}{\sqrt{3}}\cos(\zeta_n - \xi_n)\theta_n \quad (21)$$

$$l_{pnb0} = -\frac{r_s}{\sqrt{3}}\cos\left(\frac{2\pi}{3} - \zeta_n + \xi_n\right)\theta_n$$

$$l_{pnc0} = -\frac{r_s}{\sqrt{3}}\cos\left(\frac{4\pi}{3} - \zeta_n + \xi_n\right)\theta_n$$

However, to keep the proximal minimum gap length constant regardless of the rotation angle, the bending and rotation angles below in the relative coordinate need to be calculated from the bending angle $\theta_n$ and the rotation angle $\zeta_n$ in the absolute coordinate system using the procedure described above.

[Math. 42]

$$\tilde{\theta}_n, \tilde{\zeta}_n$$

These are used to calculate the driving amount of a-wire below in the relative coordinate system.

[Math. 43]

$$\tilde{l}_{pna}$$

Thereafter, calculations expressed by equations (13) to (17) in the third embodiment need to be made, which leads to an increased computational load. In this embodiment, a simple method using approximate values in absolute space is described.

First, consider that the bending angle $\theta_n$ in the n-th bending section is converted to an approximate bending angle below in the relative coordinate.

[Math. 44]

$$\tilde{\theta}_{an}$$

In the n−1-th bending section and the n-th bending section, which are two adjacent bending sections, in a case where, for example, the rotation angle $\zeta_{n-1}$ and the rotation angle $\zeta_n$ are equal to each other, the approximate bending angle in the relative coordinate needs to be expressed as follows.

[Math. 45]

$$\tilde{\theta}_{an} = \theta_n - \theta_{n-1} \quad (22)$$

On the other hand, in a case where, for example, the rotation angle $\zeta_{n-1}$ and the rotation angle $\zeta_n$ are different from each other by 90 degrees, the following holds.

[Math. 46]

$$\tilde{\theta}_{an} = \theta_n \quad (23)$$

Then, a function $\alpha$ for which the difference in the rotation angle is an argument is introduced, and the approximate bending angle in the relative coordinate needs to be calculated as follows.

$$\alpha = \cos((\zeta_n - \zeta_{n-1}) \bmod 2\pi)) \quad (24)$$

[Math. 47]

$$\tilde{\theta}_{an} = \alpha \theta_n \quad (25)$$

Next, the driving amount of a-wire in the relative coordinate system, namely,

[Math. 48]

$$\tilde{l}_{pna}$$

is calculated without using coordinate transformation. First, in this embodiment, the symbols of the wire driving displacements are defined as follows. $l_{pnam}$, $l_{pnbm}$, $l_{pncm}$: the driving displacements of a-, b-, and c-wires connected to the distal end of the n-th bending section and virtually driving the m-th bending section These are expressed as follows.

[Math. 49]

$$l_{pnam} = -\frac{r_s}{\sqrt{3}}\cos(\zeta_m - \xi_n)\theta_m \quad (26)$$

$$l_{pnbm} = -\frac{r_s}{\sqrt{3}}\cos\left(\frac{2\pi}{3} - \zeta_m + \xi_n\right)\theta_m$$

$$l_{pncm} = -\frac{r_s}{\sqrt{3}}\cos\left(\frac{4\pi}{3} - \zeta_m + \xi_n\right)\theta_m$$

When these are used, the driving amount of a-wire in the relative coordinate system of the n-th bending section, namely,

[Math. 50]

$$\tilde{l}_{pna}$$

is expressed as follows.

[Math. 51]

$$\tilde{l}_{pna} = l_{pna} - l_{pna(n-1)} \quad (27)$$

When this is substituted into equations (13) to (15) in the third embodiment, the gap length compensation amount $l_{ndd}$ is calculated. This is used, and the wire driving displacements $l_{pna}$, $l_{pnb}$, and $l_{pnc}$ are calculated by adding the sum of the gap length compensation amounts in the first to n-th sections to the wire driving displacements $l_{pna0}$, $l_{pnb0}$, and $l_{pnc0}$ used in the central-axis keeping-constant control respectively as follows.

[Math. 52]

$$l_{pna} = l_{pna0} + \sum_{m=1}^{n} l_{mdd} \quad (28)$$

$$l_{pnb} = l_{pnb0} + \sum_{m=1}^{n} l_{mdd}$$

$$l_{pnc} = l_{pnc0} + \sum_{m=1}^{n} l_{mdd}$$

As described above, the central-axis keeping-constant control as in the third embodiment can be implemented also by using an absolute coordinate system. According to this embodiment, the minimum gap length between the wire guide $164n$ in the n-th bending section nearest to the proximal side and the distal wire guide $160(n+1)$ in the adjacent bending section can also be kept constant. As a result, the accuracy of control of the continuum robot can be increased further than in the related art.

According to the present invention, it is possible to increase the accuracy of control of a continuum robot.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™) a flash memory device, a memory card, and the like.

The program and a computer-readable storage medium in which the program is stored are included in the present invention.

The above-described embodiments are only examples and can be changed or combined in various ways without departing from the technical spirit of the present invention and implemented.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A continuum robot comprising:
a first wire;
a second wire;
a distal guide configured to hold the first wire and the second wire;
a proximal guide fixed to the first wire, and slidable relative to the second wire;
a plurality of wire guides provided between the distal guide and the proximal guide;
a robot base part configured to be slidable relative to the first wire and the second wire, the robot base part being provided near the proximal guide, opposite to the plurality of wire guides;
a driving unit configured to drive the first wire and the second wire; and
a control unit configured to control the driving unit, wherein
the first wire is fixed to the plurality of wire guides,
the second wire is slidable relative to the plurality of wire guides, and
the control unit controls the driving unit so as to keep a distance between the proximal guide and the robot base part within a range of changes, wherein the range of changes is $1.0 \times 10^{-3}$ m.

2. A continuum robot comprising:
a robot base;
a distal bending section including;
a first distal wire;
a second distal wire;
a first distal guide configured to hold the first distal wire and the second distal wire;
a first proximal guide slidable relative to the first distal wire and the second distal wire;
a plurality of distal wire guides provided between the first distal guide and the first proximal guide; and
a following bending section provided between the robot base and the distal bending section, the following bending section including;
a first following wire;
a second following wire;
a second distal guide configured to hold the first following wire and the second following wire and configured such that the first distal wire and the second distal wire are slidable thereon;
a second proximal guide slidable relative to the first following wire, the second following wire, the first distal wire, and the second distal wire; and
a plurality of following wire guides provided between the second distal guide and the second proximal guide,
a driving unit configured to drive the first distal wire, the second distal wire, the first following wire, and the second following wire; and
a control unit configured to control the driving unit,
wherein the control unit controls the driving unit so as to keep a distance between the first proximal guide and the second distal guide within a range of changes, wherein the range of changes is $1.0 \times 10^{-3}$ m.

* * * * *